United States Patent
Klaveness et al.

(10) Patent No.: US 9,026,203 B2
(45) Date of Patent: May 5, 2015

(54) PHOTOSENSITIZING COMPOSITIONS

(75) Inventors: Jo Klaveness, Oslo (NO); Anders Hogset, Lysaker (NO)

(73) Assignee: PCI Biotech AS (NO)

( * ) Notice: Subject to any disclaimer, the term of this patent is extended or adjusted under 35 U.S.C. 154(b) by 0 days.

(21) Appl. No.: 13/390,404

(22) PCT Filed: Aug. 16, 2010

(86) PCT No.: PCT/GB2010/001547
§ 371 (c)(1),
(2), (4) Date: May 25, 2012

(87) PCT Pub. No.: WO2011/018635
PCT Pub. Date: Feb. 17, 2011

(65) Prior Publication Data
US 2012/0226217 A1    Sep. 6, 2012

(30) Foreign Application Priority Data
Aug. 14, 2009 (GB) .................................. 0914287.8

(51) Int. Cl.
A61K 31/409   (2006.01)
A61M 37/00    (2006.01)
C07D 487/22   (2006.01)
A61K 41/00    (2006.01)

(52) U.S. Cl.
CPC ................................ *A61K 41/0071* (2013.01)

(58) Field of Classification Search
USPC .............................. 514/410; 540/145; 604/20
See application file for complete search history.

(56) References Cited

U.S. PATENT DOCUMENTS

| | | | |
|---|---|---|---|
| 5,284,647 A | 2/1994 | Niedballa et al. | |
| 5,292,516 A | 3/1994 | Viegas et al. | |
| 5,389,681 A | 2/1995 | Galli | |
| 5,550,249 A * | 8/1996 | Della Valle et al. | 548/303.7 |
| 5,674,467 A | 10/1997 | Maier et al. | |
| 5,876,989 A | 3/1999 | Berg et al. | |
| 6,346,272 B1 | 2/2002 | Viegas et al. | |
| 6,570,013 B2 * | 5/2003 | Mylari | 544/235 |
| 6,680,301 B2 | 1/2004 | Berg et al. | |
| 7,014,839 B2 | 3/2006 | Klaveness et al. | |
| 7,223,600 B2 | 5/2007 | Berg et al. | |
| 7,287,646 B2 | 10/2007 | Gierskcky et al. | |
| 7,521,239 B2 | 4/2009 | Hogset et al. | |
| 7,662,807 B2 | 2/2010 | Rimington et al. | |
| 8,008,077 B2 | 8/2011 | Berg et al. | |
| 8,216,587 B1 | 7/2012 | Berg et al. | |
| 2003/0134813 A1 | 7/2003 | Berg et al. | |
| 2004/0259949 A1 | 12/2004 | Klaveness et al. | |
| 2006/0052433 A1 | 3/2006 | Berg et al. | |
| 2006/0282038 A1 | 12/2006 | Van Lier et al. | |
| 2011/0171184 A1 | 7/2011 | Hovig et al. | |
| 2011/0293575 A1 | 12/2011 | Hogset et al. | |
| 2012/0226217 A1 | 9/2012 | Klaveness et al. | |
| 2012/0253264 A1 | 10/2012 | Klaveness et al. | |

FOREIGN PATENT DOCUMENTS

| | | |
|---|---|---|
| EP | 0937478 A1 | 8/1999 |
| GB | 2420784 A1 | 6/2006 |
| JP | 2008095050 | 4/2008 |
| WO | 9607432 A1 | 3/1996 |
| WO | 0054708 A1 | 9/2000 |
| WO | 200054802 A2 | 9/2000 |
| WO | 0244396 A1 | 6/2002 |
| WO | 03020309 A2 | 3/2003 |
| WO | 2007021964 A2 | 2/2007 |
| WO | 2010001102 A2 | 1/2010 |
| WO | 2011018635 A2 | 2/2011 |
| WO | 2011018636 A2 | 2/2011 |

OTHER PUBLICATIONS

Stahl et al., (Handbook of Pharmaceutical Salts, 2008).*
Berg, et al.; "Site-Specific Drug Delivery by Photochemical Internalization Enhances the Antitumor Effect of Bleomycin"; Clinical Cancer Research; 11(23); pp. 8476-8485; (2005).
Cavalcante, et al.; A Combination of Techniques to Evaluate Photodynamic Efficiency of Photosensitizers; Laser Phys. Lett; 6(1); pp. 64-70; (2009).
International Search Report; International Application No. PCT/GB2010/001547; International Filing Date Aug. 16, 2010; Date of publication Jul. 7, 2011; 4 pages.
Selbo, et al.; "Photochemical Internalization Provides Time- and Space-Controlled Endolysosomal Escape of Therapeutic Molecules"; Journal of Controlled Release; 148(1); pp. 2-12; (2010).
Sengee, et al.; "Synthesis and Biological Evaluation of New Imidazolium and Piperazinium Salts of Pyropheophorbide-a for Photodynamic Cancer Therapy"; Int. J. Mol. Sci.; 9; pp. 1407-1415; (2008).
U.S. Appl. No. 13/390,360, filed Jun. 20, 2012; NonFinal Office Action; Mailed Jul. 5, 2013; 26 pages.
Berg et al.; "Site-Specific Drug Delivery by Photochemical Internalization Enhances the Antitumor Effect of Bleomycin"; Clin Cancer Res; 11; pp. 8476-8485; (2005).
Norum et al.; "Photochemical Internalization fo Bleomycin Before External-beam Radiotherapy Improves Locoregional Control in a Human Sarcoma Model"; Int J Radiat Oncol Biol Phys.; 75(3); pp. 878-885p (2009); Epub 2009).
Stahl et al.; Handbook of Pharmaceutical Salts: Properties, Selection, and Use, IUPAC, Wiley-VCH, pp. 167-169; (2008).
Berge, S.M. et al.; "Pharmaceutical Salts"; Journal of Pharmaceutical Sciences, USA, American Pharmaceutical Association; 66(1); pp. 1-19; (1977).

* cited by examiner

*Primary Examiner* — Savitha Rao
(74) *Attorney, Agent, or Firm* — Cantor Colburn LLP

(57) ABSTRACT

The invention relates to pharmaceutically acceptable salts of amphiphilic photosensitizing agents which have a water solubility of at least 0.5 mg/ml and to their use in methods of photochemical internalization. Such salts may be formed from a pharmaceutically acceptable base, for example an organic amine such as an amino alcohol, or from a pharmaceutically acceptable acid, for example a sulphonic acid or a sulphonic acid derivative. Due to their increased water solubility, such salts are particularly suitable for use in the preparation of parenteral pharmaceutical preparations, e.g. for use as solutions for injection or infusion.

4 Claims, No Drawings

PHOTOSENSITIZING COMPOSITIONS

CROSS-REFERENCE TO RELATED APPLICATIONS

This application is a 371 of PCT/GB2010/001547 filed Aug. 16, 2010, which claims the benefit of priority to GB Application No. 0914287.8, filed on Aug. 14, 2009, under the provisions of 35 U.S.C. 119 and the International Convention for the protection of Industrial Property, which are incorporated herein by reference in their entirety.

The present invention relates to photosensitizing compositions and their use in methods for the delivery of drug molecules into cells by photochemical internalization ("PCI"). More particularly, it relates to compositions for use in such methods which comprise water-soluble salts of amphiphilic photosensitizing agents and which are thus suitable for parenteral administration.

Photochemotherapy or photodynamic therapy (PDT) is a technique for the treatment of various abnormalities or disorders. PDT can be used for treatment of disorders of the skin or other epithelial organs or mucosa, especially cancer or precancerous lesions. It also finds use in the treatment of non-cancerous conditions, such as acne and age-related macular degeneration. PDT involves the application of a photosensitizing agent to the affected area of the body, followed by exposure of the area to photoactivating light in order to activate the photosensitizing agent. Activation of the photosensitizing agent converts this into a cytotoxic form which kills or otherwise reduces the proliferative potential of the affected cells.

A range of photosensitizing agents are known for use in PDT. Those known for clinical use include 5-aminolevulinic acid (5-ALA), 5-ALA methyl ester, 5-ALA hexyl ester, verteporfin, psoralens and porfimer. 5-ALA (Levulan®) and 5-ALA methyl ester (Metvix®) are used for treatment of various dermal conditions; 5-ALA hexyl ester (Hexvix®) is used for diagnosis of urinary bladder cancer; verteporfin (Visudyne®) is used for treatment of macular degeneration in the eye; and porfimer (Photofrin®) is used for treatment of lung cancer and palliative treatment of obstructive oesophageal cancer.

Photochemical internalization (also known simply as "PCI") is a drug delivery method which involves the use of light and a photosensitizing agent for introducing otherwise membrane-impermeable drugs into the cytosol of a cell, but which does not necessarily result in cell destruction or cell death. In this method, the molecule to be internalized or transferred is applied to the cells in combination with a photosensitizing agent. Exposure of the cells to light of a suitable wavelength activates the photosensitizing agent which in turn leads to disruption of intracellular compartment membranes and the subsequent release of the molecule into the cytosol. In PDT it is the effect of the light on the photosensitizing agent which forms cell-toxic materials that directly affect the disease. In contrast, in PCI, the interaction between the photosensitizing agent and light is used to affect the cell such that intracellular uptake of the drug is improved. Both mechanisms go through a pathway involving singlet oxygen species. Singlet oxygen is a highly reactive form of oxygen that can oxidize various biomolecules, including molecules in the cellular membranes. In PDT a direct-acting therapeutic agent is not normally used, while in PCI a direct-acting drug (or prodrug thereof) is always used in conjunction with the photosensitizing agent. Drugs which may be considered to be "direct-acting" are those which have an inherent biological activity (whether therapeutic or prophylactic). When present in vivo at the desired target site, such drugs do not require light to be active. The photosensitizing agents which may be used in PCI might also be used in PDT, however, not all PDT-active photosensitizers can be used in PCI.

PCI is described in the following patent documents: WO 96/07432, WO 00/54708, WO 02/44396, WO 02/44395, WO 03/020309, U.S. Pat. No. 6,680,301 and U.S. Pat. No. 5,876,989. The technology is further described in the following publications: Berg, K. et al. in Cancer Res. (1999) 59, 1180-1183, Høgset, A. et al. in Hum. Gene Ther. (2000) 11, 869-880, Prasmickaite, L. et al, in J. Gene Med. (2000) 2, 477-488, Selbo, P. K. et al. in Biochim. Biophys. Acta (2000) 1475, 307-313, Selbo, P. K. et al. in Int. J. Cancer (2000) 87, 853-859, Selbo, P. K. et al. in Int. J. Cancer (2001) 92, 761-766, Berg, K. et al. in Photodynamics News (2001) 4, 2-5, Prasmickaite, L. et al in Photochem. Photobiol. (2001) 73, 388-395, Selbo, P. K. et al. in Photochem. Photobiol. (2001) 74, 303-310, Selbo. P. K. et al in Tumor Biol. (2002) 23, 103-112, Høgset, A. et al. in Adv. Drug Deliv, Rev. (2004) 56, 95-115, Berg, K et al. in Curr. Opin. Mol. Ther. (2004) 6, 279-287, Prasmickaite, L. et al. in Expert Opin. Mol. Ther. (2004) 4, 1403-1412, Berg, K. et al. in Clin. Cancer. Res. (2005) 11, 8476-8485, Berg, K. et al. in Curr. Pharmacol. Biotech (2006) 8, 362-372 and Weyergang, A. et al. in Photochem. Photobiol. Sci. (2008) 7, 1032-1040.

Many different photosensitizing agents have been proposed for use in PCI. These include, for example, phthalocyanines such as di-sulphonated aluminium phthalocyanines (e.g. $AlPcS_2$ and $AlPcS_{2a}$); sulphonated tetraphenylporphyrins (e.g. $TPPS_{2a}$, $TPPS_4$, $TPPS_1$ and $TPPS_{2o}$); nile blue; chlorins and chlorin derivatives including bacteriochlorins and ketochlorins; uroporphyrin I; phylloerythrin; natural and synthetic porphyrins including hematoporphyrin and benzoporphyrins; methylene blue; cationic dyes; tetracyclines, naphthalocyanines; texaphyrines; pheophorbides; purpurins; rhodamines; fluoresceins; lysosomotropic weak bases; and porphycenes.

The present inventors have identified that those photosensitizing agents exhibiting amphiphilic properties and which comprise one or more charged groups are particularly suitable for use in PCI. Such agents include, in particular, the sulphonated tetraphenyl porphyrins and chlorins. However, despite the encouraging results which have been obtained when using amphiphilic photosensitizers for PCI in in vitro studies, such compounds have yet to achieve widespread clinical use.

The present inventors have recognised that a significant problem when using known amphiphilic photosensitizing agents for PCI relates to the poor solubility of the agents in solution, especially in aqueous solutions such as may be used for parenteral administration (the aqueous solubility of such agents is much less than 0.5 mg per ml). This problem has hitherto not been identified in any of the prior art literature. As will be appreciated, photosensitizers which have very low aqueous solubility have a tendency to precipitate out of solution which can result in severe side effects in vivo, especially when the photosensitizer is administered into the vascular system. These side effects can include fever and various immunological reactions and, in some cases, may be fatal. As a result, even the most potent amphiphilic photosensitizers are, at present, unsuitable for parenteral pharmaceutical preparations, e.g. for use as solutions for injection or infusion.

The inventors have now developed alternative (e.g. improved) methods of conducting PCI in vivo which involve the use of amphiphilic photosensitizing agents which are readily soluble in water and which are thus essentially free from the side-effects noted above.

Viewed from one aspect the invention thus provides a pharmaceutically acceptable salt of an amphiphilic photosensitizing agent for use in a method of photochemical internalization, wherein said salt has a water solubility of at least 0.5 mg/ml. The salt preferably has a solubility in water which exceeds 1 mg/ml, even more preferably more than 3 mg/ml or more than 5 mg/ml. Most preferably, it will have a solubility of more than 10 mg/ml.

Salts for use in the invention may have a solubility of at least 20 mg/ml, more preferably at least 25 mg/ml, e.g. at least 30 mg/ml.

The photosensitizing agents for use in the invention will be amphiphilic. As used herein, "amphiphilic" is intended to refer to the overall character of the molecule in which the extent of hydrophilicity and hydrophobicity is not constant over the entire molecule and a region of higher hydrophilicity (e.g. a polar region) is present relative to the remainder of the molecule. The photosensitizing agent will typically comprise molecules which carry one or more charged groups and which either have an overall positive (cationic) or negative (anionic) charge.

For the purposes of the invention, "water solubility" refers to solubility in water at ambient temperature, e.g. at about 20° C. Water solubility may be determined by stirring a weighed amount of solid photosensitizer with a small amount of water at 20° C. such that the solid does not completely dissolve and measuring the concentration of photosensitizer in the solution above the solid (i.e. in the supernatant solution).

The term "pharmaceutically acceptable salt" refers to a salt which retains the biological efficacy and properties of the photosensitizing agent and which is formed from a suitable non-toxic acid or base.

The terms "photochemical internalization" and "PCI" are used herein to refer to the cytosolic delivery of molecules (e.g. drug molecules) which includes the step of release of molecules from intracellular/membrane bound compartments into the cytosol of the cells of a patient.

In a further aspect the invention provides a pharmaceutically acceptable salt of an amphiphilic photosensitizing agent having a water solubility of at least 0.5 mg/ml for the preparation of a therapeutic agent for use in a method of photochemical internalization.

In a yet further aspect the invention provides a method of introducing a drug molecule into the cytosol of a cell in a patient, said method comprising the following steps:
 (a) contacting said cell with a pharmaceutically acceptable salt of an amphiphilic photosensitizing agent having a water solubility of at least 0.5 mg/ml;
 (b) contacting said cell with said drug molecule; and
 (c) irradiating said cell with light of a wavelength effective to activate the photosensitizing agent.

The photosensitizing agent to be used according to the invention may be any known photosensitizing agent having the required amphiphilic properties and which localises to intracellular compartments, particularly endosomes or lysosomes. A range of suitable agents are known in the art and described in the literature for use in PCI, including in WO 96/07432, WO 03/020309 and in GB-A-2420784. These include, in particular, the phthalocyanines such as di-sulphonated aluminium phthalocyanines (particularly those with adjacent sulphonation); sulphonated tetraphenylporphyrins (TPPS$_n$, e.g. TPPS$_{2a}$ and TPPS$_1$); chlorins and chlorin derivatives including bacteriochlorins and ketochlorins; and natural and synthetic porpyhrins including hematoporphyrin and benzoporphyrins.

The following are among the most preferred photosensitizers for use in the invention: TPCS$_{2a}$, TPPS$_{2a}$, AlPcS$_{2a}$ and porfimer (Photofrin®). Porfimer (Photofrin®) is a heterogeneous mix of substances, at least some of which are amphiphilic.

The salt for use in the invention may be formed from a pharmaceutically acceptable base such as an organic amine, in particular an amino alcohol (or alkanolamine). These compounds are capable of forming salts with anionic photosensitizers. As used herein, the term "amino alcohol" is intended to include any organic compound containing both at least one amine functional group and at least one alcohol functional group.

Alternatively, the salt for use in the invention may be a pharmaceutically acceptable acid addition salt. Suitable salt forming acids are sulphonic acids and derivatives of such acids which are capable of forming salts with cationic photosensitizers.

Suitable bases for forming salts in accordance with the invention include the amino alcohols. Such compounds may be linear, branched or cyclic. Among the amino alcohols which are particularly suitable for the preparation of the salts herein described are the lower aliphatic amino alcohols such as monoethanolamine, di-ethanolamine, tri-ethanolamine and 2-amino-2-(hydroxymethyl)propane-1,3-diol, etc. Other suitable amino alcohols include cyclic compounds such as 4-(2-hydroxyethyl)-morpholine and 1-(2-hydroxyethyl)-pyrrolidine. Particularly preferred for use in the invention are the basic salts with the amino sugars glucamine and N-methylglucamine (meglumine). Particularly preferred salts for use in the invention are the N-methylglucamine salts and ethanolamine salts.

As used herein, the term "sulphonic acid" is intended to include any organic compound containing at least one —SO$_3$H group. This may comprise 1, 2 or 3 —SO$_3$H groups, most preferably 1 or 2, e.g. 1. The term "derivatives", when used in relation to sulphonic acid is intended to encompass any such compounds containing at least one (preferably 1, 2 or 3, most preferably 1 or 2, e.g. 1) —SO$_3$X group (where X is a physiologically tolerable cation, such as a sodium, calcium, potassium, magnesium or meglumine cation).

Acid addition salts according to the invention will typically be derived from a cationic photosensitizing agent and a mono-protic sulphonic acid such as methane sulphonic acid, thereby forming a 1:1 salt. Alternatively, salts may be formed between the photosensitizer and a di- or tri-protic sulphonic acid, such as ethane-1,2-disulfonic acid. In the case where an acid having more than one acidic proton is used, the resulting salt may have a stoichiometric ratio other than 1:1, for example 2:1 (photosensitizer:acid) or 3:1 (photosensitizer:acid).

Sulphonic acids and sulphonic acid derivatives suitable for use in forming the salts according to the invention include those of formulae R—SO$_3$H (I) and R—SO$_3$X (II) in which R may be a hydrogen atom or an optionally substituted alkyl (e.g. a C$_{1-20}$ alkyl group) or aryl group (e.g. an aryl group of up to 20 carbon atoms), preferably an optionally substituted alkyl or aryl group.

As used herein, the term "alkyl" includes any long or short chain, straight-chained, branched or cyclic aliphatic, saturated or unsaturated hydrocarbon group. Optionally, this group may be substituted (e.g. mono- or poly-substituted), for example by hydroxy, alkoxy, acyloxy, nitro, alkoxycarbonyloxy, amino, aryl, oxo or halo (e.g. fluoro or chloro) groups. The unsaturated alkyl groups may be mono- or polyunsaturated and include both alkenyl and alkynyl groups.

Preferred salts for use in accordance with the invention are those formed from acids of formulae (I) or (II) in which R is an optionally substituted (i.e. mono- or poly-substituted), linear, branched or cyclic (e.g. mono- or bicyclic, bridged or non-bridged) alkyl group which may contain up to 20 carbon atoms, or an optionally substituted (i.e. mono- or poly-substituted) aryl group, which preferably contains up to 20 carbon atoms. Preferred substituents which may be present in group R include $C_{1-6}$ alkyl (e.g. methyl), hydroxy, alkoxy, acyloxy, nitro, alkoxycarbonyloxy, amino, aryl, oxo and halo (e.g. fluoro or chloro).

In general, salts according to the invention that are formed between a photosensitizing agent and a sulphonic acid compound comprise a single sulphonic acid moiety, i.e. a monoprotic acid. However, as noted above, salts formed from acids having more than one sulphonic acid moiety (e.g. 2 or 3 such groups) may also be used. Other substituents which may be present in group R therefore include one or more, preferably one, $-SO_2OH$, $-SO_2OX$ (where X is as hereinbefore defined) or $-SO_2O^-$ group. Representative examples of disulphonic acids which may be used to prepare the salts according to the invention include ethane-1,2-disulphonic acid and napthalene-1,5-disulphonic acid.

Preferred alkyl groups for group R may contain up to 20, but preferably up to 15, e.g. up to 12 carbon atoms. However, alkyl groups containing up to 10, e.g. up to 5, more preferably 1, 2 or 3 carbon atoms are preferred. In particular, linear alkyl groups having up to 10 carbon atoms are preferred, e.g. methyl, ethyl or propyl groups. Although these groups may be substituted or unsubstituted, preferably these will be unsubstituted.

Preferred aryl groups for group R include optionally substituted phenyl or napthyl groups. Preferably the aryl group is substituted, for example by one or more (e.g. by one, two or three) substituents which may include $C_{1-6}$ alkyl groups (preferably $C_{1-4}$ alkyl, e.g. methyl), alkoxy (e.g. methoxy), nitro, halo (e.g. fluoro or chloro), $-SO_3H$, $-SO_3X$ (where X is as hereinbefore defined), $-SO_2O^-$ or trifluoromethyl groups. Representative examples of aryl groups include toluene (e.g. p-toluene), benzene, napthalene and napthalene sulphonate (e.g. 2-napthalene sulphonate).

Examples of sulphonic acids suitable for forming the acids for use in the present invention include: ethane-1,2-disulphonic acid, ethanesulphonic acid, 2-hydroxy-ethanesulphonic acid, methanesulphonic acid and naphthalene-1,5-disulphonic acid.

Examples of preferred salts for use in the invention for PCI delivery of drugs include the following:
$TPCS_{2a}$ diethanolamine salt
$TPCS_{2a}$ ethanolamine salt
$TPCS_{2a}$ N-methyl-glucamine salt
$TPCS_{2a}$ triethanolamine salt
$TPCS_{2a}$ 1-(2-hydroxymethyl)-pyrrolidine salt
$TPCS_{2a}$ 2-amino-2-(hydroxymethyl)propane-1,3-diol salt
$TPPS_{2a}$ diethanolamine salt
$TPPS_{2a}$ ethanolamine salt
$TPPS_{2a}$ N-methyl-glucamine salt
$TPPS_{2a}$ triethanolamine salt
$TPPS_{2a}$ 1-(2-hydroxymethyl)-pyrrolidine salt
$TPPS_{2a}$ 2-amino-2-(hydroxymethyl)propane-1,3-diol salt
Porfimer diethanolamine salt
Porfimer ethanolamine salt
Porfimer N-methyl-glucamine salt
Porfimer triethanolamine salt
Porfimer 1-(2-hydroxymethyl)-pyrrolidine salt
Porfimer 2-amino-2-(hydroxymethyl)propane-1,3-diol salt.

The various salts herein described are themselves novel and form a further aspect of the invention. Such salts may be in the solid (e.g. powdered or granulate) state or in a dissolved or liquid (i.e. ready-to-use) form.

The salts for use in the invention may be prepared using standard processes and procedures well-known in the art. For example, these may be prepared by reaction of the desired amphiphilic photosensitizing agent with the appropriate acid or base in the presence of a suitable solvent. Such a solvent may readily be selected by those skilled in the art and typically may be water or an aqueous solution. Alternatively, the reaction may be carried out in an organic solvent in which the components are soluble such as DMSO, DMF, alcohols and acetonitrile.

In preparing the salts in accordance with the invention, the photosensitizing agent may be mixed with an aqueous or organic solvent solution of the acid or base. Typically the acid or base will be present in excess (e.g. in at least 10% excess) of an equimolar amount required for the reaction. The mixture may then be heated and, on cooling, the desired salt of the photosensitizing agent precipitates and may be recovered in solid form, e.g. by suitable techniques such as filtration. Should further purification of the salt be necessary or desirable, it may be effected by known methods such as washing with a suitable organic solvent. Suitable solvents include methanol, ethanol, isopropanol, acetone, diethyl ether, THF, ethyl acetate and mixtures thereof.

The present invention further relates to pharmaceutical compositions comprising a salt as herein described in combination with at least one pharmaceutical carrier or excipient. The pharmaceutical compositions of the invention include the unit dosage form as well as the intermediate formulations such as a powder or concentrated solution. Typically, the compositions will be provided in the form of the finished, i.e. ready-to-use, dosage forms. These include parenteral dosage forms such as an injectable solution or a solution for infusion. A unit dose of an injectable solution will generally be one vial. Preferred concentrations of the salt in parenteral solutions will be from 0.1 to 100 mg/ml, preferably from 0.5 to 50 mg/ml.

Preferably, the ready-to-use composition will be provided in the form of a solution, e.g. an aqueous solution. For example, the salt may be dissolved in a solvent selected from water, ethanol or a mixture of water and ethanol. Typically, the solvent will consist essentially of sterile water. The final solution ready for administration should preferably be isotonic or slightly hypertonic compared to blood (e.g. having an osmolality of 300 mOsm/kg or higher).

The liquid dosage forms can be made by conventional techniques known in the art. For example, the water soluble salts herein described may be dissolved in an aqueous solvent, before or after addition of any other excipients, generally with stirring and optionally at elevated temperatures. If desired, the compositions may be made initially as a concentrated solution or suspension and further diluted to the required concentration prior to use.

Although the photosensitizing agents herein described are primarily intended for parenteral administration, they may also be administered via other routes, for example through topical or oral administration. Suitable formulations for topical administration include creams and emulsions. Suitable formulations for oral administration include tablets and capsules.

The compositions may include additional excipients well known in the art, such as carriers, diluents, fillers, etc. Such excipients are typically described in Martindale's Extra Pharmacopoeia (36th Edition, 2009) and in The Merck Index (14th Edition, 2006). The most preferred excipients to be used in solutions of photosensitizers for PCI include pharmaceutically acceptable compounds which are capable of adjusting the osmolality to form isotonic solutions, antioxidants, buffers, surfactants, solvents and solubilizers. For parenteral administration, the solutions should preferably have a pH of 2-10.

The water-soluble salts herein described are particularly suitable for making liquid pharmaceutical compositions for parenteral administration. Preferably, such solutions are aqueous which means that water comprises a proportion of the solvent medium. In general, water will comprise at least 50% of the solvent, more preferably at least 60%, yet more preferably at least 80%, still more preferably at least 90%, e.g. essentially 100% of the solvent. Where another solvent other than water is present, this will typically be ethanol The compositions according to the present invention can be sterile or non-sterile. However, for most uses except external use and use in the gastrointestinal system including the oral cavity, the compositions should be sterile. Methods of sterilization include autoclaving, dry head sterilization, gamma-sterilization and treatment with ethylene oxide.

The compositions herein described may be provided in "ready-to-use" form in which the salt form of the photosensitizer is already dissolved in the aqueous solution. Alternatively, this may be provided in dry (e.g. powdered) form with instructions for dissolving this in an aqueous solution with stirring prior to use.

For use in PCI, the compositions herein described will be administered in combination with a therapeutic agent (also herein referred to as "drug molecules"). Depending on the condition to the treated, the nature of the composition, etc., the photosensitizing agents may be co-administered with the drug molecules, for example in a single composition, or they may be administered sequentially or separately.

Viewed from a further aspect the invention thus provides a product comprising a pharmaceutically acceptable salt of an amphiphilic photosensitizing agent as herein described, together with a therapeutic agent for simultaneous, separate or sequential use in a method of photochemical internalization.

Alternatively viewed, this aspect of the invention also provides a kit for use in a method of photochemical internalization comprising:
 (a) a first container containing a pharmaceutically acceptable salt of an amphiphilic photosensitizing agent as herein described;
 (b) a second container containing a therapeutic agent; and
 (c) where said salt is in solid form, a third container containing an aqueous solution for dissolving the salt prior to use.

Where the therapeutic agent is intended for co-administration with the salt of the photosensitizing agent, this may be dissolved or suspended in the same solution (e.g. an aqueous solution) prior to use.

The drug molecule to be translocated into intracellular compartments of the cells of the patient and the photosensitizing agent may be applied to the cells together or sequentially, upon which the photosensitizing compound and the molecule are endocytosed or in other ways translocated into endosomes, lysosomes or other intracellular membrane restricted compartments. The molecule to be internalized within the cell is released by exposure of the cells to light of suitable wavelengths to activate the photosensitizing compound which in turn leads to the disruption of the intracellular compartment membranes and the subsequent release of the molecule into the cytosol.

The precise timing of the addition of the molecule to be transferred (i.e. the drug molecule) and photosensitizing agent and timing of irradiation to achieve the above described effects needs to take into account various factors including the cells to be treated, the nature of the drug molecules, the environment of the cells, and whether administration is direct to the target tissue or at a distal site. Taking these considerations into account appropriate timings may readily be determined by those skilled in the art. Typically, the drug molecule and the photosensitizing agent will be contacted with the cells prior to irradiation. Light irradiation may be effected any time after administration of the photosensitizing agent. In general, the drug molecule and photosensitizing agent may be applied either simultaneously or separately from 1 to 72 hours prior to irradiation, preferably 4 to 48, e.g. 4 to 24 hours prior to irradiation.

However, irradiation may be performed before the drug molecule has been taken up into the same intracellular compartment of the cell as the photosensitizing agent (see WO 02/44396 which describes how this may be achieved in more detail), e.g. by irradiation before administration of the drug molecule, e.g. by adding the drug molecule 5 minutes to 24 hours, for example, 30 minutes to 2 hours, after irradiation.

In certain cases, the drug molecule will be administered simultaneously with the photosensitizing agent. In a further aspect the invention thus provides a pharmaceutical composition comprising a pharmaceutically acceptable salt of an amphiphilic photosensitizing agent as herein described, together with a therapeutic agent. A pharmaceutically acceptable carrier or excipient may additionally be present.

Alternatively, and more typically, the photosensitizer may be administered prior to administration of the drug molecules.

In a yet further aspect the invention provides a pharmaceutical composition comprising a pharmaceutically acceptable salt of an amphiphilic photosensitizing agent as herein described, together with a therapeutic agent, for use in therapy, e.g. for use in cancer, gene or oligonucleotide (e.g. siRNA) therapy.

In a still yet further aspect the invention provides the use of a pharmaceutically acceptable salt of an amphiphilic photosensitizing agent as herein described and/or a therapeutic agent for the preparation of a medicament for use in therapy, e.g. cancer, gene or oligonucleotide (e.g. siRNA) therapy, in which said salt of the photosensitizing agent and said therapeutic agent are contacted (either separately, simultaneously or sequentially) with cells or tissues of a patient and said cells or tissues are irradiated with light of a wavelength effective to activate said photosensitizing agent. Methods of treatment comprising such methods form further aspects of the invention.

The photosensitizing agents herein described may be used for transporting or transfecting any drug molecule into the cytosol of living cells in vivo. These may be used not only to transfer molecules (or parts or fragments thereof) into the interior of a cell but also, in certain circumstances, to present or express them on the cell surface. Thus, following transport and release of a drug molecule into the cell cytosol, if the cell(s) in question are specialised cells, such as for example antigen presenting cells, the molecule or fragment, may be transported to the surface of the cell where it may be presented on the outside of the cell, i.e. on the cell surface. Such methods have particular utility in the field of vaccination, where vaccine components, i.e. antigens or immunogens, may be introduced into a cell for presentation on the surface of that cell, in order to induce, facilitate or augment an immune response. Further details as to the utility of expressing molecules on the cell surface are described in WO 00/54802.

The drug molecules which can be introduced into the cytosol of cells using the photosensitizing agents herein described include molecules which do not readily penetrate cell membranes. Additionally, the agents herein described can increase the cytosol delivery and activity of drug molecules which are only partly able to penetrate the membrane of the cell or the membranes of intracellular vesicles. Drug molecules may be organic compounds, proteins or fragments of proteins such as for example peptides, antibodies or antigens or fragments thereof. Another class of drug molecules which may be introduced using the agents herein described are cytotoxic drugs such as protein toxins or cytotoxic organic compounds. Molecules which may be of clinical interest for treatment of cancer, but are restricted by low or no uptake into the cytosol can be introduced into the cytosol and targeted to specific cells when using the methods herein described. Gelonin is an example of such a molecule. A further example of a cytotoxic agent which may be used in conjunction with the photosensitizing agents herein described is bleomycin.

Particular forms of cancer which may be treated in accordance with the methods herein described include head and neck cancers (e.g. squamous cell carcinoma), osteosarcoma and skin metastases, in particular those originating from breast cancers.

Depending on the nature of the drug molecule, the methods herein described may be used for treating various disorders, such as rheumatoid arthritis, artherosclerosis and other cardiovascular diseases, virus and other infections, psoriasis, solar keratosis, wound healing, fracture healing, warts and inherited genetic disorders such as cystic fibrosis, Gorlin's syndrome and ataxia telangiectasia.

Another class of appropriate drug molecules are nucleic acids. Nucleic acids may be used in the form of genes encoding for example therapeutic proteins, antisense RNA molecules, ribozymes, RNA aptamers, short hairpin RNAs (shRNAs), microRNAs or triplex forming oligonucleotides. Alternatively the nucleic acids may be employed in the form of non-encoding molecules such as for example synthetic DNA or RNA antisense molecules, ribozymes, siRNAs, microRNAs, aptamers, triplex forming oligonucleotides, peptide nucleic acids (PNAs), transcription factor "decoy" DNA or chimeric oligonucleotides for repair of specific mutations in the patient. Where appropriate the nucleic acid molecules may be in the form of whole genes or nucleic acid fragments optionally incorporated into a vector molecule e.g. a plasmid or a viral vector. The latter form has particular applicability when the transfer molecule is to be used in methods of gene therapy in which genes are therapeutically transferred to a patient's cells. This may be used in treating many diseases such as cancer, cardiovascular diseases, viral infections, and monogenic disorders such as cystic fibrosis.

Optionally, one or other or both of the pharmaceutically acceptable salt of the photosensitizing agent and the drug molecule to be introduced into the cells may be attached to or associated with or conjugated to carrier molecules, targeting molecules or vectors which can act to facilitate or increase the uptake of the photosensitizing agent or the drug molecule or can act to target or deliver these entities to a particular cell type, tissue or intracellular compartment. Examples of carrier systems include polylysine, chitosans, polyethylenimines or other polycations, dextran sulphate, different cationic lipids, liposomes, reconstituted LDL-particles or sterically stabilised liposomes. These carrier systems can generally improve the pharmacokinetics and increase the cellular uptake of the drug molecule and/or the photosensitizing agent and may also direct the drug molecule and/or the photosensitizing agent to intracellular compartments that are especially beneficial for obtaining photochemical internalization, but they do not generally have the ability to target the drug molecule and/or the photosensitizing agent to specific cells (e.g. cancer cells) or tissues. However, to achieve such specific or selective targeting the carrier molecules, the drug molecule and/or the photosensitizer may be associated with, bound or conjugated to specific targeting molecules that will promote the specific cellular uptake of the drug molecule into desired cells or tissues. Such targeting molecules may also direct the drug molecule to intracellular compartments that are especially beneficial for obtaining photochemical internalization.

Many different targeting molecules can be employed, e.g. as described in Curiel, D. T. (1999), Ann. New York Acad. Sci. 886, 158-171; Bilbao, G. et al. (1998), in Gene Therapy of Cancer (Walden et al., eds., Plenum Press, New York), Peng K. W. and Russell S. J. (1999), Curr. Opin. Biotechnol. 10, 454-457; and Wickham T. J. (2000), Gene Ther. 7, 110-114.

The carrier molecule and/or the targeting molecule may be associated, bound or conjugated to the drug molecule, to the photosensitizing agent or both, and the same or different carrier or targeting molecules may be used. Such targeting molecules or carriers may also be used to direct the drug molecule to particular intracellular compartments especially beneficial for the employment of PCI, for example lysosomes or endosomes.

The compositions of the invention may be formulated in conventional manner with one or more physiologically acceptable carriers or excipients according to techniques well known in the art. The nature of the composition and carriers or excipient materials, dosages etc. may be selected in routine manner according to choice and the desired route of administration, purpose of treatment, etc. Dosages may likewise be determined in routine manner and may depend upon the nature of the drug molecule, purpose of treatment, age of patient, mode of administration, etc.

Compositions will generally be administered topically or systemically. Topical compositions include gels, creams, ointments, sprays, lotions, pessaries, aerosols, drops, solutions and any of the other conventional pharmaceutical forms in the art. Topical administration to inaccessible sites may be achieved by techniques known in the art, e.g. by the use of catheters or other appropriate drug delivery systems.

Preferably, the compositions may be provided in a form adapted for parenteral administration, for example by intradermal, subcutaneous, intraperitoneal or intravenous injection, or by infusion. Alternative pharmaceutical forms thus include suspensions and solutions containing the salt of the photosensitizing agent optionally together with one or more inert conventional carriers and/or diluents. Formulations for parenteral administration may be in the form of aqueous or non-aqueous, isotonic, sterile injection solutions or suspensions. These solutions may be prepared from sterile powders or granules using one or more carriers or excipients, for example, suitable dispersing, wetting or suspending agents. Suitable carriers for the preparation of solutions for injection include water, saline and dextrose. Other non-toxic parenterally acceptable diluents or solvents may be used, including amino acid solutions, such as Glavamin® (Fresenius Kabi), carbohydrate solutions such as Glucos® (Braun), electrolytes such as sodium chloride solutions, Ringer's solution, trometamol solutions, or mixtures of any of the foregoing.

The total dose, concentration and administration volume of photosensitizer and drug will vary over a large range depending on several factors. The main factors are: indication (nature of the disease), stage of disease, organ system and choice of photosensitizer and drug.

The concentration of the compounds as described hereinbefore in the compositions depends upon the intended use of the compound, the nature of the composition, mode of administration, the condition to be treated and the patient and may be varied or adjusted according to choice. For use in PCI, it is important that the concentration of the photosensitizing agent is such that once taken up into the cell, e.g. into, or associated with, one or more of its intracellular compartments and activated by irradiation, one or more cell structures are disrupted, e.g. one or more intracellular compartments are lysed or disrupted. The photosensitizing agents may be used at a concentration of, for example, 0.5 to 100 mg per ml. For in vivo human treatments the photosensitizing agent may be used in the range 0.05-20 mg/kg body weight when administered systemically or 0.1-20% in a solvent for topical application. The time of incubation of the cells with the photosensitizing agent (i.e. the "contact" time) can vary from a few minutes to several hours, e.g. even up to 48 hours or longer. The time of incubation should be such that the photosensitizing agent is taken up by the appropriate cells. The incubation of the cells with the photosensitizing agent may optionally be followed by a period of incubation with photosensitizer free medium before the cells are exposed to light and/or the drug molecule is administered.

Determining the appropriate doses of drug molecules for use in accordance with the present invention is routine practice for a person skilled in the art. Where the drug molecule is a protein or peptide, the drug molecules would generally be used at doses of less than 5 mg/kg (e.g. 0.1-5 mg/kg). Where the drug molecule is a nucleic acid, approximately $10^{-6}$-1 g nucleic acid per injection may be used in humans.

Following administration of a compound or composition as herein described the area treated is exposed to light to achieve the desired effect. The light irradiation step to activate the photosensitizing agent may be effected according to techniques and procedures well known in the art. Suitable light sources capable of providing the desired wavelength and light intensity are also well known in the art. The time for which the body surface or cells are exposed to light in the methods of the present invention may vary. For example, the efficiency of the internalization of the drug molecule into the cytosol appears to increase with increased exposure to light. Generally, the length of time for the irradiation step is in the order of minutes to several hours, e.g. preferably up to 60 minutes e.g. from 1 to 30 minutes, e.g. from 0.5 to 3 minutes or from 1 to 5 minutes or from 1 to 10 minutes e.g. from 3 to 7 minutes, and preferably approximately 3 minutes, e.g. 2.5 to 3.5 minutes. Appropriate light doses can be selected by a person skilled in the art and will depend on the amount of photosensitizer accumulated in the target cells or tissues. The irradiation will in general be applied at a dose level of 40 to 200 Joules/cm$^2$, for example at 100 Joules/cm$^2$ at a fluence range of less than 200 mW/cm$^2$. Irradiation with wavelengths of light in the range 500-750 nm, e.g. 550 to 700 nm, is particularly suitable for in vivo use in the methods herein described.

Methods for irradiation of different areas of the body, e.g. by lamps or lasers are well known in the art (see for example Van den Bergh, Chemistry in Britain, May 1986 p. 430-439). For inaccessible regions this may conveniently be achieved using optical fibres. For some uses, various devices such as catheters may be required for light delivery to areas of interest.

The invention will now be described in more detail by way of the following non-limiting Examples:

Example 1

Preparation of Meso-Tetraphenyl Porphyrin Disulphonate bis(monoethanolamine) ((MEA)$_2$-TPPS$_{2a}$)

Meso-tetraphenyl porphyrin disulphonate bis(triethylamine) prepared from the free acid was dissolved in methanol and an excess of ethanolamine added. The solution was stirred for 15 minutes before the solvent was removed in vacuo at 30° C. with a rotary evaporator. This procedure was repeated two more times.

Example 2

Preparation of Meso-Tetraphenyl Porphyrin Disulphonate bis(meglumate) ((Megl)$_2$-TPPS$_{2a}$)

Meso-tetraphenyl porphyrin disulphonate (200 mg, 0.26 mmol) was added to a solution of N-methyl-D-glucamine (102 mg, 0.52 mmol) in de-ionized water (5 ml) at room temperature. The mixture was stirred for 15 minutes and the mixture was freeze-dried overnight. The title compound was isolated as a dark red solid material. Yield: 310 mg (100%).

Example 3

Preparation of Meso-Tetraphenyl Porphyrin Disulphonate bis(tris(hydroxymethyl)methylamine) ((TRIS)$_2$-TPPS$_{2a}$)

Meso-tetraphenyl porphyrin disulphonate (200 mg, 0.26 mmol) was added to a solution of tris(hydroxymethyl)methylamine (63 mg, 0.52 mmol) in de-ionized water (5 ml) at room temperature. The mixture was stirred for 15 minutes and the mixture was freeze-dried overnight. The title compound was isolated as a dark red solid material. Yield: 260 mg (100%).

Example 4

Preparation of Meso-Tetraphenyl Porphyrin Disulphonate bis(diethanolamine) ((DEA)$_2$-TPPS$_{2a}$)

Meso-tetraphenyl porphyrin disulphonate (100 mg, 0.13 mmol) was added to a solution of diethanolamine (27 mg, 0.26 mmol) in de-ionized water (5 ml) at room temperature. The mixture was stirred for 15 minutes and the mixture was freeze-dried overnight. The title compound was isolated as a dark red solid material. Yield: 103 mg (80%).

Example 5

Preparation of Meso-Tetraphenyl Porphyrin Disulphonate bis(1-(2-hydroxyethyl)pyrrolidine) ((HEP)$_2$-TPPS$_{2a}$)

Meso-tetraphenyl porphyrin disulphonate (100 mg, 0.13 mmol) was added to a solution of 1-(2-hydroxyethyl)pyrrolidine) (30 mg, 0.26 mmol) in de-ionized water (5 ml) at room temperature. The mixture was stirred for 15 minutes and the mixture was freeze-dried overnight. The title compound was isolated as a dark red solid material. Yield: 117 mg (90%).

Example 6

Preparation of Meso-Tetraphenyl Porphyrin Disulphonate bis(triethanolamine) ((TEA)$_2$-TPPS$_{2a}$)

Meso-tetraphenyl porphyrin disulphonate (100 mg, 0.13 mmol) was added to a solution of triethanolamine (39 mg, 0.26 mmol) in de-ionized water (5 ml) at room temperature. The mixture was stirred for 15 minutes and the mixture was freeze-dried overnight. The title compound was isolated as a dark red solid material. Yield: 106 mg (79%).

Example 7

Preparation of Meso-Tetraphenyl Chlorin Disulphonate bis(monoethanolamine) (((MEA)$_2$-TPCS$_{2a}$)

Meso-tetraphenyl porphyrin disulphonate bis(triethylamine) prepared from the free acid was dissolved in methanol and an excess of ethanolamine added. The solution was stirred for 15 minutes before the solvent was removed in vacuo at 30° C. with a rotary evaporator. This procedure was repeated two more times.

Example 8

Preparation of Meso-Tetraphenyl Chlorin Disulphonate bis(meglumate) ((Megl)$_2$-TPCS$_{2a}$)

Meso-tetraphenyl chlorin disulphonate (100 mg, 0.13 mmol) was added to a solution of N-methyl-D-glucamine (51 mg, 0.26 mmol) in de-ionized water (5 ml) at room temperature. The mixture was stirred for 15 minutes and the mixture was freeze-dried overnight. The title compound was isolated as a dark red solid material. Yield: 157 mg (100%).

Example 9

Preparation of Meso-Tetraphenyl Chlorin Disulphonate bis(tris(hydroxymethyl)methylamine) ((TRIS)$_2$-TPCS$_{2a}$)

Meso-tetraphenyl chlorin disulphonate (100 mg, 0.13 mmol) was added to a solution of tris(hydroxymethyl)methylamine (31 mg, 0.26 mmol) in de-ionized water (5 ml) at room temperature. The mixture was stirred for 15 minutes and the mixture was freeze-dried overnight. The title compound was isolated as a dark red solid material. Yield: 157 mg (100%).

Example 10

Solubility of Meso-Tetraphenyl Porphyrin Disulphonate Salts (TPPS$_{2a}$)

Water was added in 0.2 ml portions to the various salts described in Examples 1 to 6 (approx. 50 mg) in a test tube. The mixture was agitated until solid particles were broken up and dissolved.

| Example No. | Compound | Minimum solubility in water |
|---|---|---|
| 1 | (MEA)$_2$-TPPS$_{2a}$ | 42.3 mg/ml |
| 2 | (Megl)$_2$-TPPS$_{2a}$ | 89.7 mg/ml |
| 3 | (TRIS)$_2$-TPPS$_{2a}$ | 49.9 mg/ml |
| 4 | (DEA)$_2$-TPPS$_{2a}$ | 31.4 mg/ml |
| 5 | (HEP)$_2$-TPPS$_{2a}$ | 28.3 mg/ml |
| 6 | (TEA)$_2$-TPPS$_{2a}$ | 32.1 mg/ml |

Highly concentrated solutions of TPPS$_{2a}$ salts were viscous.

Example 11

Solubility of Meso-Tetraphenyl Chlorin Disulphonate Salts (TPCS$_{2a}$)

Water was added in 0.2 ml portions to the various salts described in Examples 7 to 9 (approx. 50 mg) in a test tube. The mixture was agitated until solid particles were broken up and dissolved.

| Example No. | Compound | Minimum solubility in water |
|---|---|---|
| 7 | (MEA)$_2$-TPCS$_{2a}$ | 34.9 mg/ml |
| 8 | (Megl)$_2$-TPCS$_{2a}$ | 38.9 mg/ml |
| 9 | (TRIS)$_2$-TPCS$_{2a}$ | 32.1 mg/ml |

Highly concentrated solutions of TPPS$_{2a}$ salts were viscous.

Example 12

Stability of Meso-Tetraphenyl Porphyrin Disulphonate Salts (TPPS$_{2a}$)

Aqueous solutions of TPPS$_{2a}$ salts (approx. 1% weight) were kept at 40° C. for 31 days. The solutions were analyzed by HPLC (HP 1100). The HPLC conditions were as follows:
Column: Agilent Extend C-18
Mobile phase: 85% methanol, 15% water
Flow: 1.0 ml per minute
Detector: UV detector, 415 nm

| Example No. | Compound | Degradation |
|---|---|---|
| 1 | (MEA)$_2$-TPPS$_{2a}$ | No degradation |
| 2 | (Megl)$_2$-TPPS$_{2a}$ | No degradation |
| 3 | (TRIS)$_2$-TPPS$_{2a}$ | No degradation |
| 4 | (DEA)$_2$-TPPS$_{2a}$ | No degradation |
| 5 | (HEP)$_2$-TPPS$_{2a}$ | No degradation |
| 6 | (TEA)$_2$-TPPS$_{2a}$ | No degradation |

Conclusion: all samples were stable at 40° C. for 31 days.

Example 13

Stability of Meso-Tetraphenyl Chlorin Disulphonate Salts (TPCS$_{2a}$)

Aqueous solutions of TPCS$_{2a}$ salts (approx. 1% weight) were kept at 40° C. for 31 days. The solutions were analyzed by HPLC (HP 1100) according to the method used in Example 12.

| Example No. | Compound | Degradation |
|---|---|---|
| 7 | (MEA)$_2$-TPCS$_{2a}$ | No degradation |
| 8 | (Megl)$_2$-TPCS$_{2a}$ | No degradation |
| 9 | (TRIS)$_2$-TPCS$_{2a}$ | No degradation |

Conclusion: all samples were stable at 40° C. for 31 days.

Example 14

Capsule Containing (MEA)$_2$-TPPS$_{2a}$ for Oral Administration (MEA)$_2$-TPPS2a (30 mg) from Example 1 was mixed volumetrically with lactose monohydrate 0.15 mm (900 mg) (Apotekproduksjon AS, Oslo, Norway) using a mortar and pestle. The powder was filled into a hard gelatin capsule no. 000 (Apotekproduksjon AS, Oslo, Norway).

Example 15

Isotonic Sterile Solution of (Tris)$_2$-TPCS$_{2a}$ without Surfactants (TRIS)$_2$-TPCS$_{2a}$ (30 mg) from Example 9 was dissolved in saline (0.9% sodium chloride) (1.0 ml) using a mixer (3M ESP CapMix) for 2 minutes. The brown solution was free from particulates (examined by microscopy).

Example 16

Kit Comprising (TRIS)$_2$-TPCS$_{2a}$ and Solvent

A kit was made comprising two vials:
Composition of vial A: (TRIS)$_2$-TPCS$_{2a}$ (20 mg) from Example 9 as dry powder in a vial (100 ml)
Composition of vial B: An aqueous solution (52 ml) comprising:

| | |
|---|---|
| Sodium chloride | 120 mM |
| Potassium dihydrogen phosphate | 4.3 mM |
| Dipotassium hydrogenphosphate | 4.3 mM |
| HCl/NaOH | q.s. ad pH 6.0 |
| Water for injection | q.s |

The solution in vial B was added to vial A, and vial A was shaken by hand for 3 minutes. The solution should be free from visible particles before use.

Example 17

Topical Formulation Comprising (TRIS)$_2$-TPCS$_{2a}$ for Administration onto the Skin or Mucosa (TRIS)$_2$-TPCS$_{2a}$ (20 mg) from Example 9 was mixed volumetrically with Unguentum Merck using a mortar and pestle. The brown cream comprising 4 mg (TRIS)$_2$-TPCS$_{2a}$ per ml was filled in a glass vial.

Example 18

Emulsion Formulation Comprising (TRIS)$_2$-TPCS$_{2a}$ for Parenteral or Enteral Administration (TRIS)$_2$-TPCS$_{2a}$ (24 mg) from Example 9 was dissolved in a lipid emulsion (ClinOleic 200 mg/ml (20%) from Baxter) using a mixer (3M ESP CapMix) for 2 minutes. The brown emulsion was free from (TRIS)$_2$-TPCS$_2$, particulates (examined by microscopy).

Example 19

Formulation Containing Tetraphenyl Chlorin Disulphonate bis(monoethanolamine) ((MEA)$_2$-TPCS$_{2a}$) with Cremophor (MEA)$_2$-TPCS$_{2a}$ from Example 7 was formulated in aqueous 10% Cremophor ELP to concentrations of 30 or 60 mg/ml according to the following procedure:
(MEA)$_2$-TPCS$_{2a}$ was weighed in a container;
Cremophor ELP was heated to 60-70° C.;
The heated Cremophor was added to the (MEA)$_2$-TPCS$_{2a}$ under stirring conditions;
The solution was stirred for approximately 5 minutes at 60-70° C. and pre-heated (to 60-70° C.) sterile water was slowly added until the Cremophor concentration was 10%. The solution was kept at 60-70° C. during the whole procedure; and
The solution was then autoclaved.

The 30 mg/ml formulation may be used for intravenous administration, for example with a starting dose of 0.25 mg/kg body weight.

Example 20

Formulation Containing Tetraphenyl Chlorin Disulphonate bis(monoethanolamine) ((MEA)$_2$-TPCS$_{2a}$) in Tween 80

(MEA)$_2$-TPCS$_{2a}$ was formulated in 3% Tween 80 according to the following procedure:
(MEA)$_2$TPCS$_{2a}$ was weighed into a bottle;
50 mM Tris buffer (pH 8.5) was added to the bottle and the solution stirred (500-700 rpm) for 10 minutes;
Tween 80 was added and the solution stirred (500-700 rpm) for 10 minutes. The final concentration of Tween 80 in the formulation was 3%;
Mannitol was added and the solution stirred (500-700 rpm) for 20 hours. The final concentration of mannitol in the formulation was 2.8%;
The 30 mg/ml (MEA)$_2$TPCS$_{2a}$ formulation was filtered with a 0.22 μm filter to remove particles;
The formulation was filled into vials with stoppers and caps;
The formulation was then autoclaved for 20 minutes at 121° C.

The formulation should be stored at 2-8° C. protected from light.

Example 21

Clinical Phase I/II Study in Cancer Patients

In a phase I/II clinical study cancer patients were administered the photosensitizer TPCS$_{2a}$ (30 mg/ml of the diethanolamine salt ((MEA)$_2$-TPCS$_{2a}$) in an aqueous formulation of 10% Cremophor ELP (see Example 19). 11 patients in 3 groups were given doses of respectively 0.25, 0.5 and 1.0 mg TPCS$_{2a}$ per kg body weight 4 days before illumination (652 nm wavelength, 60 J/cm$^2$) of a defined target tumour. In addition, the patients received an intravenous injection of the cytotoxic agent bleomycin (15 000 IU per m$^2$ body surface) 3 hours before illumination. The TPCS$_{2a}$ formulation was administered as a slow intravenous injection and the patients experienced no pain or other administration-related adverse reactions; this is in contrast to the use of other photosensitizers (e.g. temoporfin) formulated in non-aqueous formulations where the administration can be associated with strong pain. The aqueous formulation also made it possible to flush the injection needle and vein with saline after photosensitizer injection, thereby eliminating the unwanted effect of photosensitivity at or near to the injection site which is often observed for photosensitizers in non-aqueous formulations where such flushing is not possible.

The patient population included patients with head and neck cancers (squamous cell carcinoma), osteosarcoma and skin metastases of breast cancer. Complete clinical regression of the target tumour was induced in all patients a few weeks after treatment, showing that TPCS$_{2a}$-mediated photochemical internalisation of bleomycin constitutes an efficient treatment of solid tumours, across several different tumour types.

Example 22

Tablet Composition Comprising $(MEA)_2$-$TPPS_{2a}$ for Oral Administration

| | |
|---|---|
| $(MEA)_2$-$TPPS_{2a}$ | 100 mg |
| Microcrystalline cellulose | 800 mg |
| Crosscaramellose(Na) (AcDiSol) | 30 mg |
| Magnesium stearate | 30 mg |

All ingredients were blended. A tablet was compressed (tablet diameter: 13 mm; tablet weight: 960 mg).

The invention claimed is:

1. A method of photochemical internalization comprising administering to a patient in need thereof a pharmaceutically acceptable salt of an amphiphilic photosensitizing agent, wherein said salt has a water solubility of at least 30 mg/ml, and wherein said salt selected from $TPCS_{2a}$ diethanolamine salt, $TPCS_{2a}$ ethanolamine salt, $TPCS_{2a}$ trithanolamine salt, $TPPS_{2a}$ diethanolamine salt, $TPPS_{2a}$ ethanolamine salt and $TPPS_{2a}$ trithanolamine salt.

2. The method of claim 1, wherein said pharmaceutically acceptable salt of an amphiphilic photosensitizing agent is administered simultaneously, separately, or sequentially together with a therapeutic agent.

3. The method of claim 2, wherein said therapeutic agent is bleomycin.

4. A method of introducing a drug molecule into the cytosol of a cell in a patient, said method comprising:
 (a) contacting said cell with a pharmaceutically acceptable salt of an amphiphilic photosensitizing agent, wherein said salt has a water solubility of at least 30 mg/ml, and wherein said salt is selected from $TPCS_{2a}$ diethanolamine salt, $TPCS_{2a}$ ethanolamine salt, $TPCS_{2a}$ trithanolamine salt, $TPPS_{2a}$ diethanolamine salt, $TPPS_{2a}$ ethanolamine salt and $TPPS_{2a}$ trithanolamine salt;
 (b) contacting said cell with said drug molecule; and
 (c) irradiating said cell with light of a wavelength effective to activate the photosensitizing agent.

* * * * *